United States Patent
Zhu et al.

(10) Patent No.: US 8,094,903 B2
(45) Date of Patent: Jan. 10, 2012

(54) SYSTEM AND METHOD FOR CORONARY DIGITAL SUBTRACTION ANGIOGRAPHY

(75) Inventors: Ying Zhu, Monmouth Junction, NJ (US); Wei Zhang, Plainsboro, NJ (US); Adrian Barbu, Tallahassee, FL (US); Simone Prummer, Neunkirchen am Brand (DE); Martin Ostermeier, Buckenhof (DE); Dorin Comaniciu, Princeton Junction, NJ (US)

(73) Assignee: Siemens Aktiengesellschaft, Munich (DE)

(*) Notice: Subject to any disclaimer, the term of this patent is extended or adjusted under 35 U.S.C. 154(b) by 880 days.

(21) Appl. No.: 12/157,837

(22) Filed: Jun. 13, 2008

(65) Prior Publication Data
US 2009/0010512 A1  Jan. 8, 2009

Related U.S. Application Data

(60) Provisional application No. 60/946,738, filed on Jun. 28, 2007.

(51) Int. Cl.
*G06K 9/03* (2006.01)

(52) U.S. Cl. ...... 382/130; 382/131; 382/132; 378/98.12

(58) Field of Classification Search .................. 382/128, 382/130, 131, 132; 378/42, 98.12
See application file for complete search history.

(56) References Cited

U.S. PATENT DOCUMENTS

| | | | |
|---|---|---|---|
| 5,557,684 A | 9/1996 | Wang et al. | |
| 5,647,360 A * | 7/1997 | Bani-Hashemi et al. | 600/425 |
| 6,154,518 A * | 11/2000 | Gupta | 378/62 |
| 6,826,292 B1 | 11/2004 | Tao et al. | |
| 6,987,865 B1 | 1/2006 | Szeliski et al. | |
| 7,155,032 B2 | 12/2006 | Szeliski et al. | |
| 7,551,721 B2 * | 6/2009 | Nakaura et al. | 378/98.12 |
| 7,583,831 B2 * | 9/2009 | Tu et al. | 382/131 |
| 7,817,834 B2 * | 10/2010 | Bernhardt et al. | 382/129 |
| 7,826,884 B2 * | 11/2010 | Baumgart | 600/407 |
| 7,940,971 B2 * | 5/2011 | Zhang et al. | 382/128 |
| 2006/0285747 A1 | 12/2006 | Blake et al. | |
| 2007/0116356 A1 | 5/2007 | Gong et al. | |

OTHER PUBLICATIONS

Barbu, A., et al., "Hierarchical Learning of Curves Application to Guidewire Localization in Fluoroscopy", IEEE Int'l. Conf. Comp. Vision and Pattern Rec., 2007.
Coleman, T.F., et al., "A Reflective Newton Method for Minimizing a Quadractic Function Subject to Bounds on some of the Variables", SIAM Journal on Optimization, 1996.
Comaniciu, D., "Nonparametric Information Fusion for Motion Estimation", IEEE Conf. Comp. and Pattern Rec., 2003.
Freeman, W.T., et al., "The Design and Use of Steerable Filters", IEEE Transactions on Pattern Analysis and Machine Intelligence, 1991.
Tu, Z., "Probabilistic Boosting-Tree: Learning Discriminative Models for Classification, Recognition, and Clustering", IEEE Int'l. Conf. Comp. Vision, 2006.

* cited by examiner

Primary Examiner — Allen C. Ho

(57) ABSTRACT

A method and system for extracting coronary vessels fluoroscopic image sequences using coronary digital subtraction angiography (DSA) are disclosed. A set of mask images of a coronary region is received, and a sequence of contrast images for the coronary region is received. For each contrast image, vessel regions are detected in the contrast image using learning-based vessel segment detection and a background region of the contrast image is determined based on the detected vessel regions. Background motion is estimated between one of the mask images and the background region of the contrast image, and the mask image is warped based on the estimated background motion to generate an estimated background layer. The estimated background layer is subtracted from the contrast image to extract a coronary vessel layer for the contrast image.

23 Claims, 6 Drawing Sheets

SYSTEM AND METHOD FOR CORONARY DIGITAL SUBTRACTION ANGIOGRAPHY

This application claims the benefit of U.S. Provisional Application No. 60/946,738, filed Jun. 28, 2007, the disclosure of which is herein incorporated by reference.

BACKGROUND OF THE INVENTION

The present invention relates to fluoroscopic image sequences, and more particularly to detecting coronary vessel layers from fluoroscopic image sequences.

Angiography is a medical imaging technique in which X-ray images are used to visualize internal blood filled structures, such as arteries, veins, and the heart chambers. Since blood has the same radiodensity as the surrounding tissues, these blood filled structures cannot be differentiated from the surrounding tissue using conventional radiology. Thus, in angiography, a contrast agent is added to the blood, usually via a catheter, to make the blood vessels visible via X-ray. In many angiography procedures, X-ray images are taken over a period of time, which results in a sequence of fluoroscopic images, which show the motion of the blood over the period of time. Such fluoroscopic image sequences contain useful information that can be difficult to decipher due to the collapsing of 3-dimensional information into the 2-dimensional images.

In traditional computer imaging problems of motion estimation, occlusion handling or motion segmentation are typically the main concerns. Accordingly, traditional techniques for extracting objects of interest from image sequences typically use intensity based approaches to differentiate between objects in the image sequences. However, such traditional techniques can yield erroneous results in medical image sequences, such as fluoroscopic image sequences, which are generated using the phenomenon of transparency. Since various internal structures have different levels of transparency in the fluoroscopic images, these structures can overlap, and it may be difficult to accurately distinguish between these structures in the fluoroscopic image sequences using the traditional intensity based approaches.

BRIEF SUMMARY OF THE INVENTION

The present invention provides a method and system for extracting coronary vessels from fluoroscopic image sequences using coronary digital subtraction angiography (DSA). Embodiments of the present invention provide real-time extraction of coronary vessel layers for each frame of a fluoroscopic image sequence.

In one embodiment of the present invention, a set of mask images is received. The set of mask images is a sequence of fluoroscopic images of a coronary region taken over at least one full cardiac cycle with no contrast medium injected into the vessels. A sequence of contrast images is then received. The contrast images are fluoroscopic images of the coronary region with a contrast medium injected into the coronary vessels. For each contrast image, vessel regions are detected in the contrast image using learning-based vessel segment detection and a background region of the contrast image is determined based on the detected vessel regions. One of the mask images that best matches the background region of the contrast image is selected, and background motion is estimated between the selected mask image and the background region of the contrast image. The mask image is then warped based on the estimated background motion to generate an estimated background layer. The estimated background layer is subtracted from the contrast image to extract a coronary vessel layer for the contrast image.

These and other advantages of the invention will be apparent to those of ordinary skill in the art by reference to the following detailed description and the accompanying drawings.

DETAILED DESCRIPTION OF EXEMPLARY EMBODIMENTS

Figure 1:
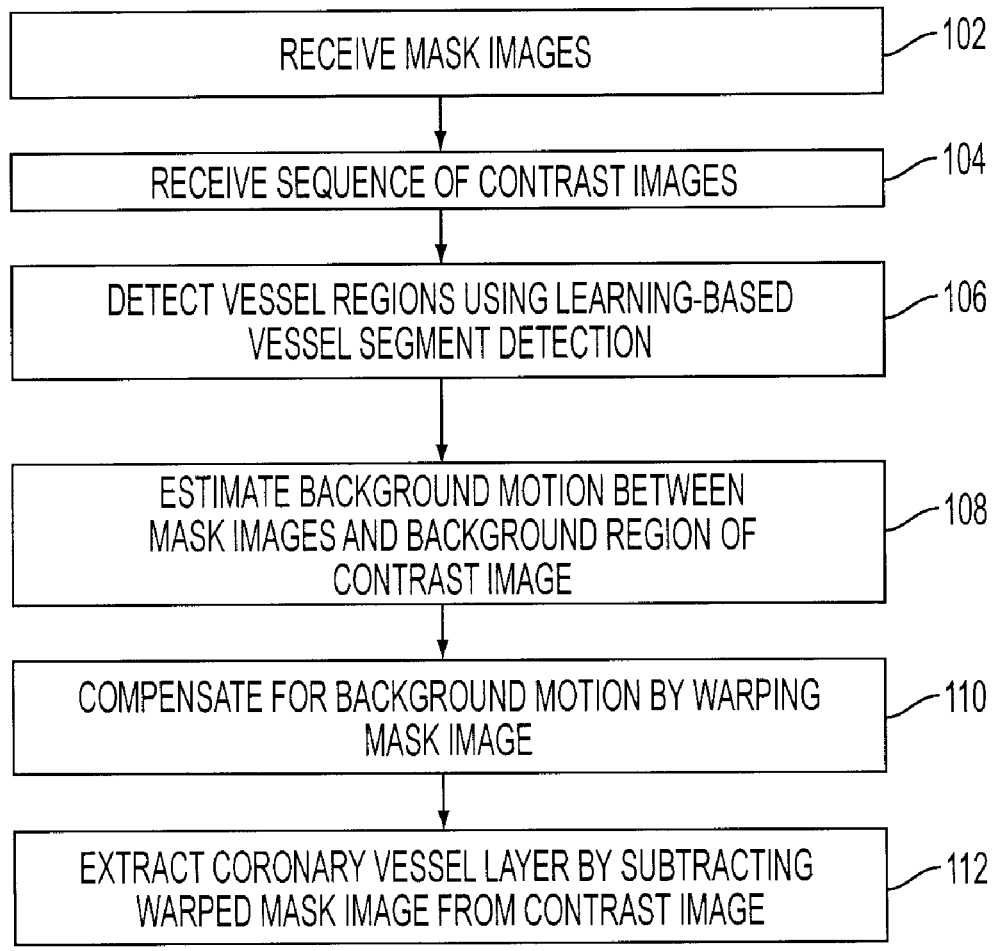
FIG. 1 illustrates a method for extracting coronary vessels from a fluoroscopic image sequence using coronary digital subtraction angiography (DSA)

The present invention is directed to a method for detecting coronary vessel layers from fluoroscopic images. Embodiments of the present invention are described herein to give a visual understanding of the coronary vessel layer extraction method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Digital subtraction angiography (DSA) is a technique for visualizing blood vessels in the human body. In DSA, a sequence of fluoroscopic images, referred to as contrast images, is acquired to show the passage of contrast medium that is injected into the vessel of interest. A sequence of fluoroscopic images contains multiple 2D X-ray images obtained in real time. The X-ray images record a certain field of view of a time period. Accordingly, motion of objects within the field of view can be observed in a sequence of fluoroscopic images. The background structures are largely removed from the contrast images by subtracting a mask image, which is an image acquired before contrast injection. However, the appearance of background structures in a contrast image and a mask image can differ due to fluctuation of radiation, acquisition noise, and patient motion. The difference between the background structures in the contrast images and the mask image can cause errors in detecting the blood vessels.

The main cause of differences in the appearance of background structures in a contrast image and a mask image is patient motion. Motion correction for DSA can involve various techniques for image motion estimation, where the motion between a contrast image and a mask image is obtained by warping one image to match the other. Commonly used matching criteria for motion estimation include optimization of various similarity or error measures, such as normalized cross-correlation, sum of absolute values of differences, variance of differences, etc. In the case of coronary DSA, cardiac motion causes more severe differences between contrast images and mask images. Furthermore, because of the complexity of cardiac motion, the commonly used matching criteria are often violated in image regions of coronary vessels, making it more difficult to estimate the background motion around coronary vessels in coronary DSA.

United States Publication No. 2008/0025588, issued as U.S. Pat. No. 7,940,971, describes a method for coronary DSA in which a motion layer approach is used to separate a layer of coronary vessels from other image layers. This approach uses layer decomposition, which requires the number of layers and the motion of each layer to be known a priori in order to recover different layers. However, the motion of the coronary vessels is complex and non-rigid, and hence, is difficult to recover, especially with thin vessels. Furthermore, in order to perform the layer decomposition for a current frame (2D X-ray image), previous and subsequent frames are used, which means this technique may be impractical for real-time applications.

Embodiments of the present invention provide a viable approach to coronary DSA that combines robust motion estimation and learning-based object detection to achieve fully automatic and real-time coronary vessel detection. Embodiments of the present invention formulate coronary DSA as a problem to remove dynamic background structures from a contrast image. A background layer $B(x)$ is defined as a transparent image layer containing background structures, i.e., structures other than coronary vessels. A foreground layer $F(x)$ is defined as a transparent image layer containing coronary vessels with contrast injection. The compositional model of a contrast image $I_t(x)$ is defined as:

$$\log I_t(x) = \log B(x + v_{B,t}(x)) + \log F(x + v_{F,t}(x)) \quad (1)$$

where $v_B(x)$ and $v_F(x)$ are motions of the background and foreground layers respectively. In mask images, only background layer is visible due to absence of contrast medium. Thus, the compositional model of a mask image $I_m(x)$ is defined as:

$$\log I_m(x) = \log B(x + v_{B,m}(x)) \quad (2)$$

In order to detect the coronary vessels, coronary DSA obtains the foreground layer $F(x + v_{F,t}(x))$ by subtracting the background layer $B(x + v_{B,t}(x))$ from the contrast image $I_t(x)$. Since the compositional model is additive in the logarithmic domain, in the following discussion, $I_m(x)$, $I_t(x)$ are used to denote the logarithmic images.

Figure 2:
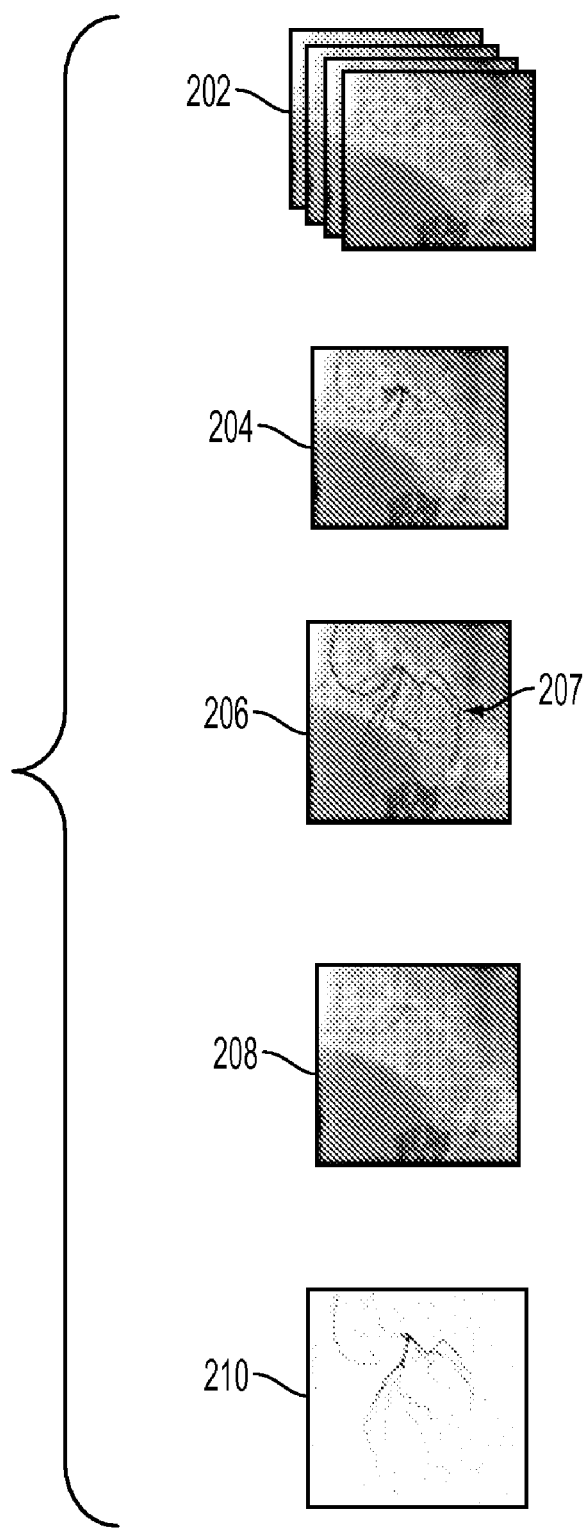
FIG. 2 illustrates exemplary images resulting from the steps of the method of FIG. 1.

FIG. 1 illustrates a method for extracting coronary vessels from a fluoroscopic image sequence using coronary DSA. The method of FIG. 1 utilizes learning-based object detection to facilitate the estimation of background motion. FIG. 2 illustrates exemplary images resulting from the steps of the method of FIG. 1. The images of FIG. 1 are referred to below while describing the method steps of FIG. 1.

At step 102, multiple mask images are received. The mask images are fluoroscopic or X-ray images of a coronary region of a patient without any contrast agent injected into the coronary vessels. The mask images are a sequence taken over the course of at least one cardiac cycle (heartbeat). Accordingly, the cardiac motion over the course of a full cardiac cycle is implicitly embedded in the set of mask images, such that background structures in various cardiac phases are captured in the set of mask images. The mask images can be received by acquiring the mask images directly from an X-ray scanning device. It is also possible that the mask images can be received by loading mask images that were previously acquired images and stored, for example, on a computer readable medium or storage of a computer system. When the set of mask images is received, the mask images are stored on a memory or storage of a computer system that is implementing the method of FIG. 1. As illustrated in FIG. 2, images 202 show a set of mask images.

At step 104, a sequence of contrast images is received. The sequence of contrast images can be electronic data representing fluoroscopic or X-ray images resulting from an X-ray procedure, such as an angiograph, in which a contrast agent is injected into the coronary vessels. The sequence of contrast images are images of the coronary region taken at a regular interval over a time frame. Each image in the sequence can be referred to as a frame. The contrast images can be received directly from an X-ray scanning device, or previously stored contrast images can be loaded. The sequence of contrast images are processed frame by frame to independently extract the coronary vessels for each contrast image in the sequence. Accordingly, steps 106-112 of FIG. 1 are performed independently for each contrast image in the sequence. These steps can be automatically performed for each contrast image in real-time as each contrast image in the sequence is received. Image 204 of FIG. 2 shows an exemplary contrast image.

Figure 3:
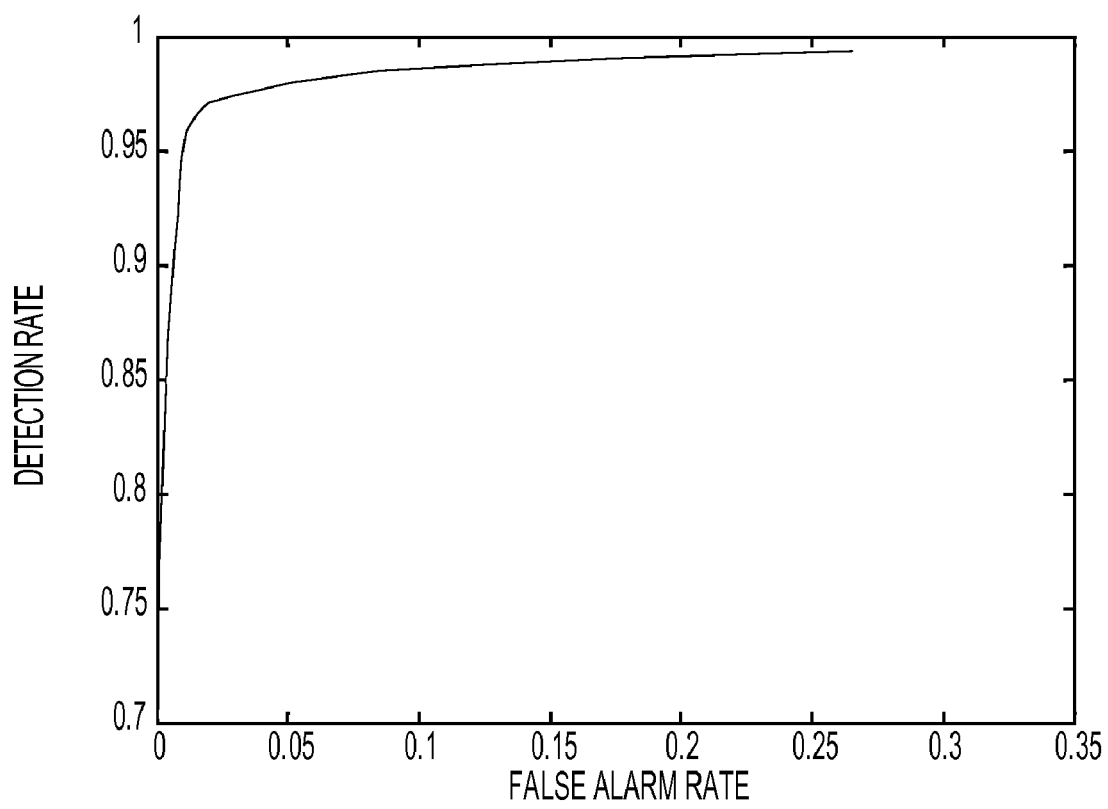
FIG. 3 illustrates Receiver Operation Characteristics (ROC) of an exemplary binary classifier.

At step 106, vessel regions in the contrast image are detected using learning-based vessel segment detection. In order to detect vessel regions in the contrast image, a vessel segment detector can be implemented using a binary classifier that is learned from a set of vessel images and non-vessel images using a probabilistic boosting tree algorithm. Given an image patch $I_0$, the binary classifier calculates the conditional probability that a vessel segment appears in this image patch $p(vessel|I_0)$. The vessel segment detector is applied for various vessel orientations and thicknesses at various image locations, and the conditional probability is obtained as a function of vessel location, orientation, and thickness. By accepting detections with the condition probability above a certain threshold, image regions with presence of coronary vessels can be obtained. Such image regions are referred to herein as detected vessel regions $\Omega$. The detected vessel regions $\Omega$ can then be excluded from the contrast image. The remaining image region $\Omega^C$ is primarily background structures, and is referred to herein as the background region of the contrast image. Image 206 of FIG. 2 illustrates vessel regions 207 detected in the contrast image 204 using an exemplary binary classifier. The exemplary binary classifier used to detect the vessel regions 207 was trained using 2779 examples of vessel image patches extracted from 94 contrast frames and 6079 examples of non-vessel image patches extracted from 159 frames. FIG. 3 illustrates the Receiver Operation Characteristics (ROC) of the exemplary binary classifier.

Figure 4:
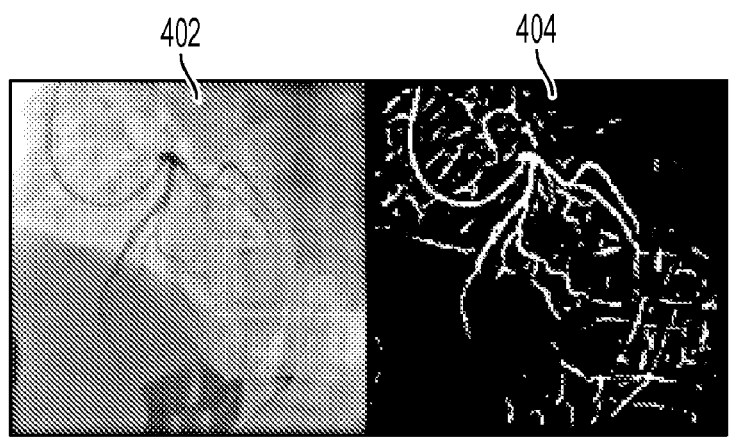
FIG. 4 illustrates ridge features extracted using steerable filters for an exemplary contrast image.

In order to speed up vessel detection for a contrast image, it is possible to apply a set of efficient steerable filters to identify ridge features in the contrast image, and then perform the vessel detection using the binary classifier only at the ridge features. FIG. 4 illustrates ridge features extracted using steerable filters for an exemplary contrast image. As illustrated in FIG. 4, image 402 is an exemplary contrast image, and image 404 shows ridge features extracted from contrast image 402 using a set of steerable filters. Accordingly, in order to detect the vessel regions of contrast image 402, it is possible to perform vessel detection using the binary classifier only on the ridge features shown in image 404.

Returning to FIG. 1, at step 108, background motion is estimated between each of the mask images and the background region of the contrast image. As described above the background region $\Omega^C$ of the contrast image is obtained by excluding the detected vessel regions $\Omega$ from the original contrast image. The background region $\Omega^C$ of the contrast image is then compared to each of the mask images in order to determine background motion between the background region $\Omega^C$ and each mask image and select one of the mask images that best matches the background region $\Omega^C$ of the contrast image. The best mask image can be selected using an optimal matching criterion for motion estimation. In order to select the best mask image, a dense motion field is estimated between each mask image and the background region of the contrast image. The mask images are warped according to the estimated motion field to match the background region of the contrast image. The best mask image is selected such that the mean-squared-error between its warped image and the background region of the contrast image is minimum. Since the set of mask images represent a full cardiac cycle, the selected mask image is the mask image obtained at the most similar point in the cardiac cycle as the contrast image.

The motion field is estimated between the masks image and the background region $\Omega^C$ of the contrast image using robust motion estimation. A robust motion estimation method is described in D. Comaniciu, "Nonparametric Information Fusion for Motion Estimation", IEEE Conf. Computer Vision and Pattern Recognition (CVPR'03), Madison, Wis., Vol. 1, 59-66, 2003, which is incorporated herein by reference. Such a robust motion estimation method can be adapted to estimate the background motion between the background region of the contrast image $I_t(x):x\in\Omega^C$ and a mask image $I_m(x)$, using the equation:

$$\hat{v}_t(x) = \underset{v_B}{\operatorname{argmin}} \|I_t(x) - I_m(x + v_B(x))\|^2_{x\in\Omega^C}. \quad (3)$$

The motion estimation method first solves the above brightness constancy equation, and then covariance-based fusion can be applied to obtain a final estimate of a dense motion field. Essentially, the mask image is a background layer consisting of various background structures. These background structures undergo non-rigid motion and are seen again in a contrast image. By estimating a dense motion field between a mask image and the background region of a contrast image, a mask image is related to a contrast image through background motion. The exclusion of the detected vessel regions serves the purpose of eliminating the influence from the foreground layer in background motion estimation. Accordingly, the motion field estimated using the motion estimation algorithm between the selected best mask image and the background region of the contrast image is the estimated background motion.

At step 110, the selected mask image is warped to compensate for the estimated motion between the mask image and the background region of the contrast image in order to generate an estimated background layer of the contrast image. Accordingly, once the background motion field $\hat{v}_t(x)$ between the background region of the contrast image and the mask image is estimated, the background layer $\hat{B}_t(x)$ of the contrast image can be estimated by warping the image based the mask image, such that:

$$\hat{B}_t(x) = I_m(x+v_B(x)) \quad (4)$$

Image 208 of FIG. 2 illustrates the estimated background layer of contrast image 204.

At step 112, the coronary vessel layer is extracted from the contrast image by subtracting the warped mask image from the contrast image. Accordingly, once the estimated background layer $\hat{B}_t(x)$ is generated, the foreground layer $\hat{F}_t(x)$, or coronary vessel layer, is obtained by background subtraction, such that:

$$\hat{F}_t(x) = I_t(x) - \hat{B}_t(x). \quad (5)$$

Image 210 of FIG. 2 illustrates the coronary vessel layer (foreground layer) of contrast image 204. The extracted coronary vessel layer can be output by displaying the coronary vessel layer as an image on a display device, storing the coronary vessel layer in storage or memory of a computer system, etc.

Figure 5:
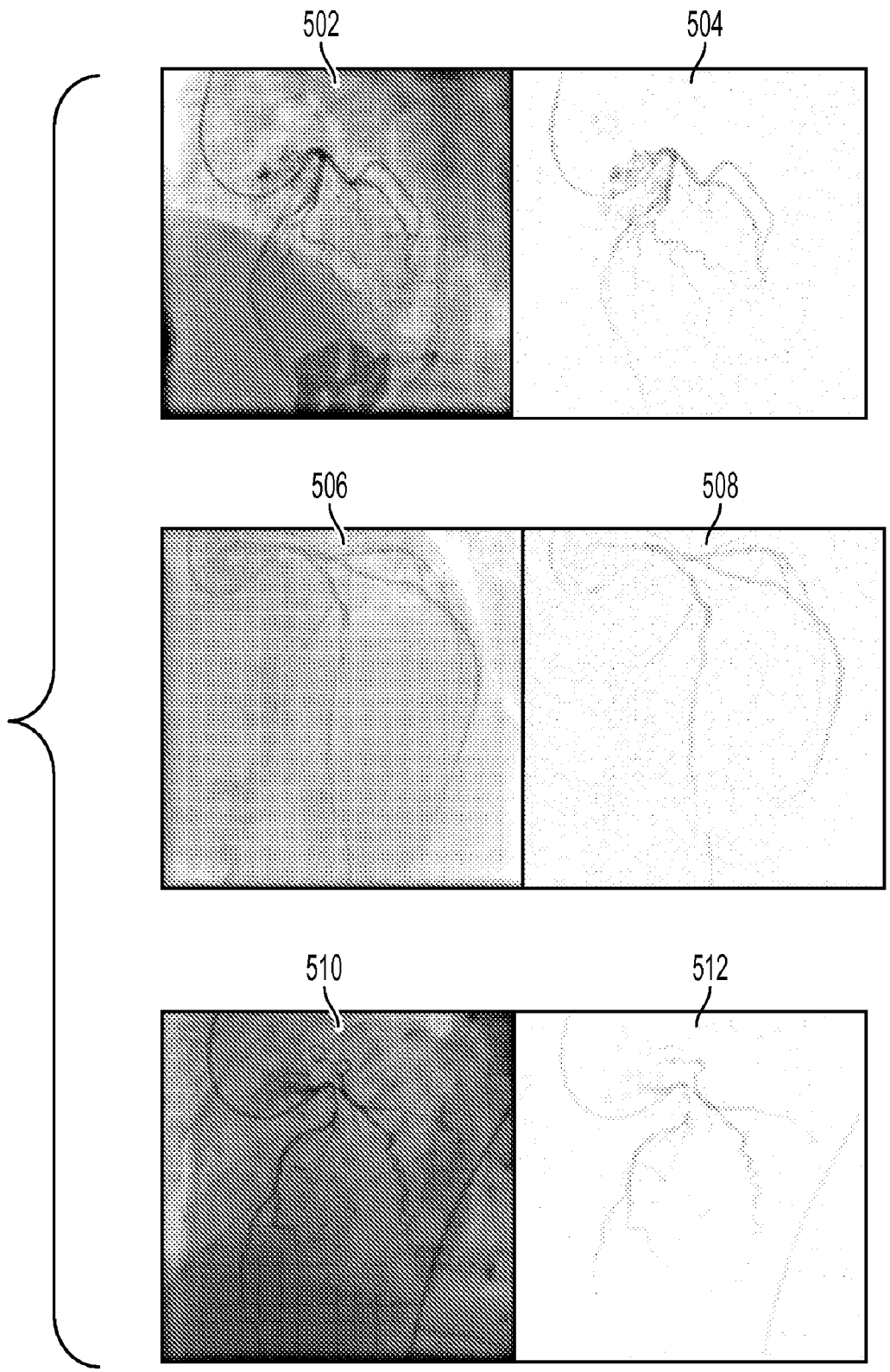
FIG. 5 illustrates exemplary results of the coronary DSA method of FIG. 1.

FIG. 5 illustrates exemplary results of the coronary DSA method of FIG. 1. As illustrated in FIG. 5, images 502, 506, and 510 are original contrast images and images 504, 508, and 512 are coronary vessel layers extracted from contrast images 502, 506, and 510, respectively.

Once the coronary vessel layers are extracted from the contrast images using the coronary DSA method of FIG. 1, it is possible to virtually enhance the coronary vessels. This is a direct clinical application of the coronary DSA method can save contrast medium and lower radiation. In order to enhance the coronary vessels, the brightness of pixels in the detected coronary vessel layer (foreground layer) is decreased in the original contrast image. Accordingly, an enhanced contrast image can be obtained as:

$$I_t(x) = \hat{B}_t(x) + \lambda \hat{F}_t(x) \quad (6)$$

Figure 6:
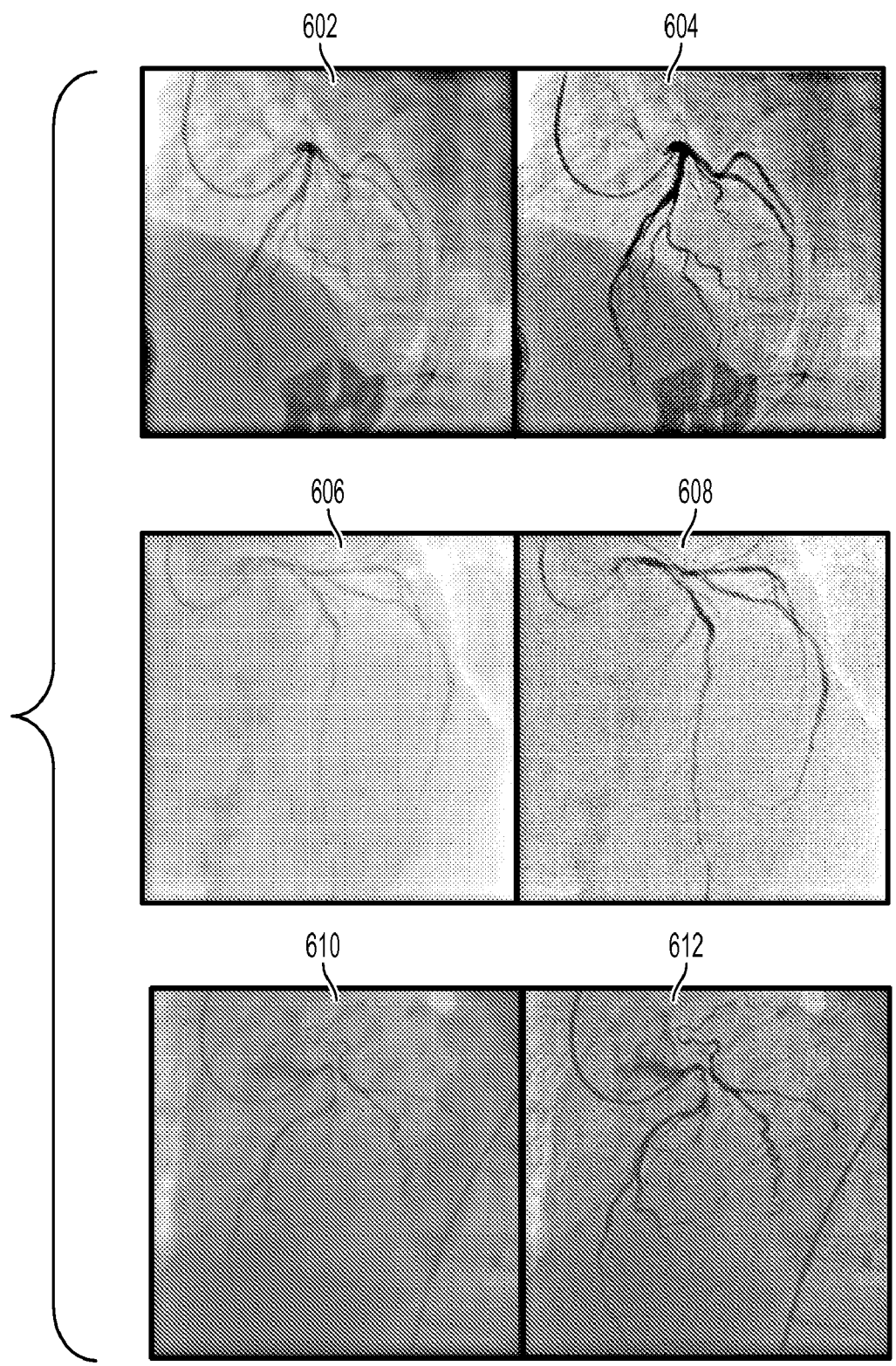
FIG. 6 illustrates exemplary contrast images having enhanced coronary vessels.

FIG. 6 illustrates exemplary contrast images having enhanced coronary vessels. As illustrated in FIG. 6, images 602, 606, and 610 are original contrast images and images 604, 608, and 612 are enhanced contrast images resulting from enhancing the extracted coronary vessels in contrast images 602, 606, and 610, respectively.

Figure 7:
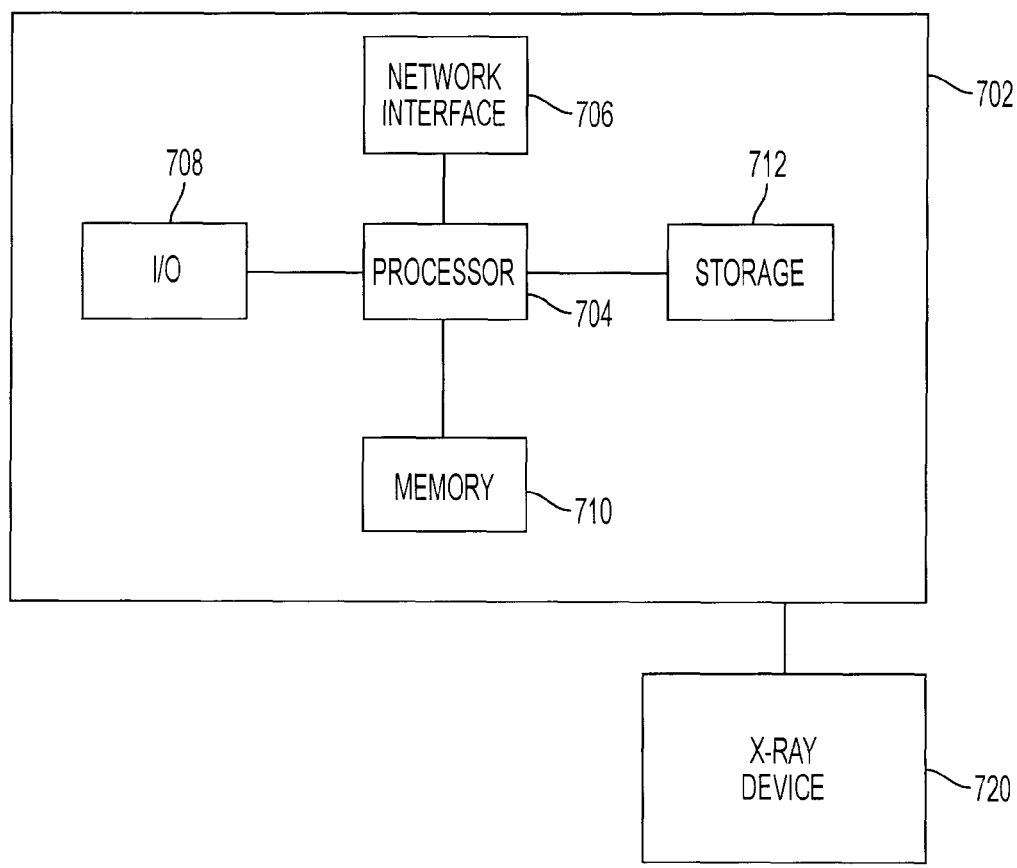
FIG. 7 is a high level block diagram of a computer capable of implementing the present invention.

The above-described methods for extracting coronary vessel layers from a sequence of fluoroscopic contrast images may be implemented on a computer using well-known computer processors, memory units, storage devices, computer software, and other components. A high level block diagram of such a computer is illustrated in FIG. 7. Computer 702 contains a processor 704 which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, applications for performing the above-described method steps of the method of FIG. 1 can be defined by the computer program instructions stored in the memory 710 and/or storage 712 and controlled by the processor 704 executing the computer program instructions. Furthermore, sets of mask images, sequences of contrast images, and output coronary vessel layers and background layers can be stored in the storage 712 and/or the memory 710. The computer 702 also includes one or more network interfaces 706 for communicating with other devices via a network. An X-ray device 720 can be connected to the computer 702 to input the contrast images and the mask images to the computer 702. It is possible to implement the X-ray device 720 and the computer 702 as one device. It is also possible that the X-ray device 720 and the computer 702 communicate wirelessly through a network. The computer 702 also includes other input/output devices 708 that enable user interaction with the computer 702 (e.g., display, keyboard, mouse, speakers, buttons, etc.) One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for extracting coronary vessels from a contrast image, comprising:
    receiving a plurality of mask images of a coronary region;
    receiving a contrast image of the coronary region;
    detecting vessel regions in the contrast image using learning-based vessel segment detection;
    determining a background region of the contrast image based on the detected vessel regions;
    estimating background motion between one of the plurality of mask images and the background region of the contrast image;
    warping said one of the plurality of mask images based on the estimated background motion to generate an estimated background layer; and
    extracting a coronary vessel layer from the contrast image by subtracting the estimated background layer from the contrast image.

2. The method of claim 1, further comprising:
    repeating said steps of receiving a contrast image, detecting vessel regions in the contrast image, determining a background region of the contrast image, estimating background motion, warping one of the plurality of mask images, and extracting a coronary vessel layer from the contrast image for each of a sequence of contrast images.

3. The method of claim 2, wherein the coronary vessel layer for each of the sequence of contrast images is extracted in real-time as each of the sequence of contrast images is received.

4. The method of claim 1, wherein the plurality of mask images comprises a sequence of mask images of the coronary region taken over at least one full cardiac cycle.

5. The method of claim 1, wherein said step of detecting vessel regions in the contrast image comprises:
    applying a set of steerable filters to the contrast image to detect ridge features in the contrast image; and
    detecting vessel segments at the detected ridge features using a learned binary classifier.

6. The method of claim 1, wherein said step of determining a background region of the contrast image based on the detected vessel regions comprises:
    excluding the detected vessel regions from the contrast image to generate the background region of the contrast image.

7. The method of claim 1, wherein said step of estimating background motion between one of the plurality of mask images and the background region of the contrast image comprises:
    estimating a motion field between each mask image and the background region of the contrast image; and
    selecting one of the plurality of mask images that best matches the background region of the contrast image based on the estimated motion fields between each of the plurality of mask images and the background region of the contrast image.

8. The method of claim 1, further comprising:
    enhancing coronary vessels in the contrast image based on the extracted coronary vessel layer.

9. An apparatus for extracting coronary vessels from a contrast image, comprising:
    means for receiving a plurality of mask images of a coronary region;
    means for receiving a contrast image of the coronary region;
    means for detecting vessel regions in the contrast image using learning-based vessel segment detection;
    means for determining a background region of the contrast image based on the detected vessel regions;
    means for estimating background motion between one of the plurality of mask images and the background region of the contrast image;
    means for warping said one of the plurality of mask images based on the estimated background motion to generate an estimated background layer; and
    means for extracting a coronary vessel layer from the contrast image by subtracting the estimated background layer from the contrast image.

10. The apparatus of claim 9, wherein said means for receiving a contrast image of the coronary region comprises:
    means for receiving a sequence of contrast images of the coronary region.

11. The apparatus of claim 9, wherein the plurality of mask images comprises a sequence of mask images of the coronary region taken over at least one full cardiac cycle.

12. The apparatus of claim 9, wherein said means for detecting vessel regions in the contrast image comprises:
    means for applying a set of steerable filters to the contrast image to detect ridge features in the contrast image; and
    means for detecting vessel segments at the detected ridge features using a learned binary classifier.

13. The apparatus of claim 9, wherein said means for determining a background region of the contrast image based on the detected vessel regions comprises:
    means for excluding the detected vessel regions from the contrast image to generate the background region of the contrast image.

14. The apparatus of claim 9, wherein said means for estimating background motion between one of the plurality of mask images and the background region of the contrast image comprises:
    estimating a motion field between each mask image and the background region of the contrast image; and
    selecting one of the plurality of mask images that best matches the background region of the contrast image based on the estimated motion fields between each of the plurality of mask images and the background region of the contrast image.

15. The apparatus of claim 9, further comprising:
    means for enhancing coronary vessels in the contrast image based on the extracted coronary vessel layer.

16. A non-transitory computer readable medium encoded with computer executable instructions for extracting coronary vessels from a contrast image, the computer executable instructions defining steps comprising:
    receiving a plurality of mask images of a coronary region;
    receiving a contrast image of the coronary region;
    detecting vessel regions in the contrast image using learning-based vessel segment detection;

determining a background region of the contrast image based on the detected vessel regions;

estimating background motion between one of the plurality of mask images and the background region of the contrast image;

warping said one of the plurality of mask images based on the estimated background motion to generate an estimated background layer; and extracting a coronary vessel layer from the contrast image by subtracting the estimated background layer from the contrast image.

17. The non-transitory computer readable medium of claim 16, further comprising computer executable instructions defining the step of:

repeating said steps of receiving a contrast image, detecting vessel regions in the contrast image, determining a background region of the contrast image, estimating background motion, warping one of the plurality of mask images, and extracting a coronary vessel layer from the contrast image for each of a sequence of contrast images.

18. The non-transitory computer readable medium of claim 17, wherein the coronary vessel layer for each of the sequence of contrast images is extracted in real-time as each of sequence of contrast images is received.

19. The non-transitory computer readable medium of claim 16, wherein the plurality of mask images comprises a sequence of mask images of the coronary region taken over at least one full cardiac cycle.

20. The non-transitory computer readable medium of claim 16, wherein the computer executable instructions defining the step of detecting vessel regions in the contrast image comprise computer executable instructions defining the steps of:

applying a set of steerable filters to the contrast image to detect ridge features in the contrast image; and detecting vessel segments at the detected ridge features using a learned binary classifier.

21. The non-transitory computer readable medium of claim 16, wherein the computer executable instructions defining the step of determining a background region of the contrast image based on the detected vessel regions comprise computer executable instructions defining the step of:

excluding the detected vessel regions from the contrast image to generate the background region of the contrast image.

22. The non-transitory computer readable medium of claim 16, wherein the computer executable instructions defining the step of estimating background motion between one of the plurality of mask images and the background region of the contrast image comprise computer executable instructions defining the steps of:

estimating a motion field between each mask image and the background region of the contrast image; and selecting one of the plurality of mask images that best matches the background region of the contrast image based on the estimated motion fields between each of the plurality of mask images and the background region of the contrast image.

23. The non-transitory computer readable medium of claim 16, further comprising computer executable instructions defining the step of:

enhancing coronary vessels in the contrast image based on the extracted coronary vessel layer.

* * * * *